United States Patent [19]

Peclard

[11] 4,109,650
[45] Aug. 29, 1978

[54] RESERVOIR WITH HANDLE AND COVER

[75] Inventor: Michel Peclard, Fianarantsoa, Madagascar

[73] Assignee: Les Products Associes LPA SA, Switzerland

[21] Appl. No.: 674,151

[22] Filed: Apr. 6, 1976

[30] Foreign Application Priority Data

Apr. 8, 1975 [CH] Switzerland .............. 004422/75

[51] Int. Cl.² ........................................... A61H 9/00
[52] U.S. Cl. ................................ 128/66; 128/62 A; 222/162
[58] Field of Search .............. 128/66, 229, 227, 272.3, 128/274, 62 A, 65; 141/355, 352, 360, 362, 363, 115; 222/508, 162

[56] References Cited

U.S. PATENT DOCUMENTS

| 3,107,029 | 10/1963 | Rylander | 220/85 H |
|---|---|---|---|
| 3,155,092 | 11/1964 | McNair | 128/66 |
| 3,393,673 | 7/1968 | Mattingly | 128/66 |
| 3,425,410 | 2/1969 | Cammack | 128/66 |
| 3,495,587 | 2/1970 | Freedman | 128/66 |
| 3,762,411 | 10/1973 | Lloyd et al. | 128/66 X |
| 3,765,574 | 10/1973 | Urquiza | 222/465 X |
| 3,783,867 | 1/1974 | Summersby et al. | 128/66 X |
| 3,871,560 | 3/1975 | Crippa | 128/62 A X |

Primary Examiner—Robert W. Michell
Assistant Examiner—Michael H. Thaler
Attorney, Agent, or Firm—Kane, Dalsimer, Kane, Sullivan and Kurucz

[57] ABSTRACT

A buccal hygiene apparatus which includes a casing enclosing a hydraulic pump and motor unit. A handpiece is connected to the casing by a flexible tubing. A reservoir is removably fittable on the casing in a position for supplying water to the pump and motor unit via an outlet in the bottom of the reservoir. The outlet includes a valve for closing it when the reservoir is removed from the casing and opening it when the reservoir is fitted on the casing. A reservoir is provided with a gripping member and is of smaller dimensions than the casing.

6 Claims, 6 Drawing Figures

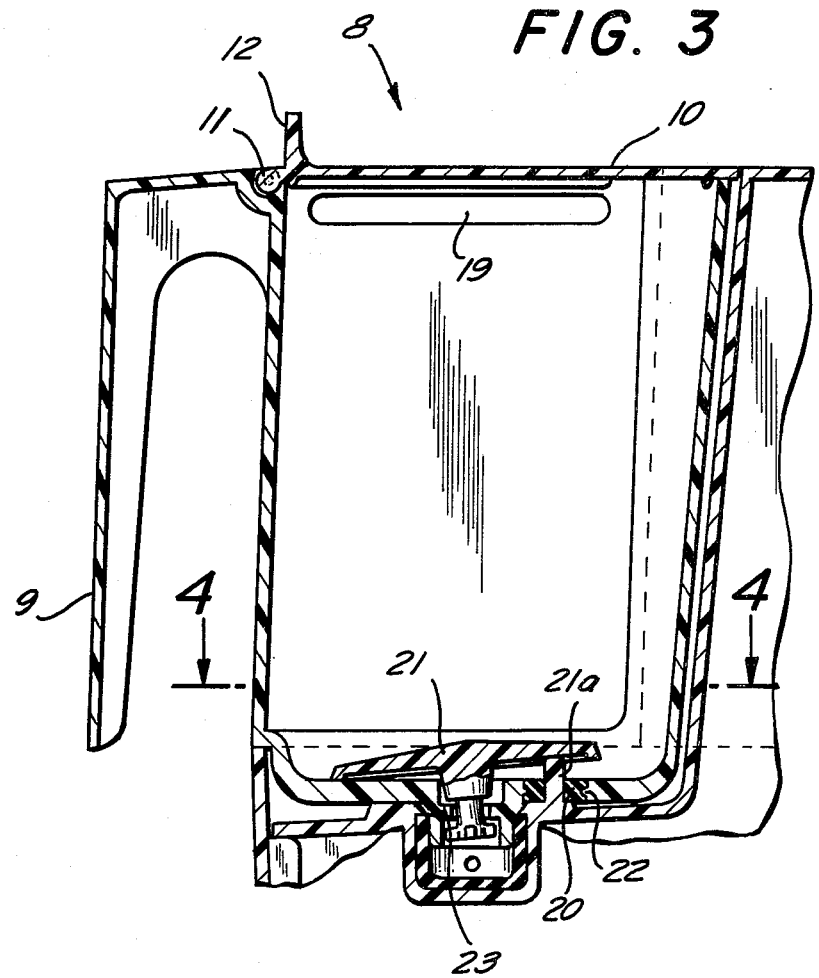
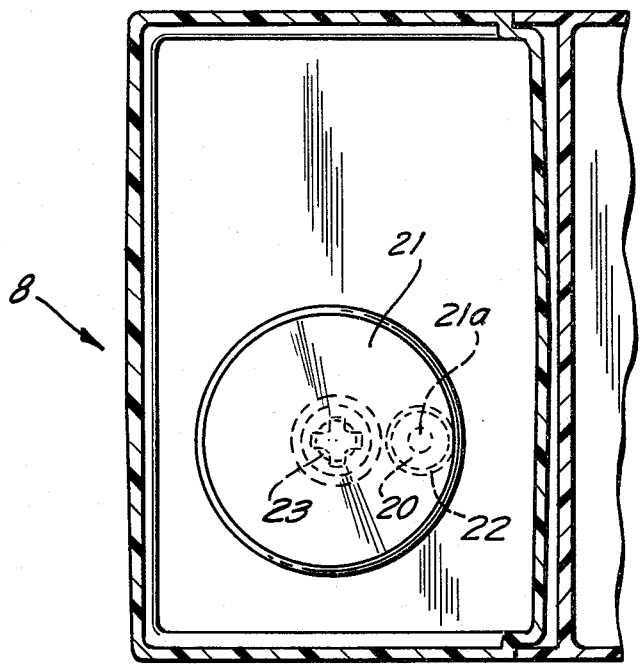

RESERVOIR WITH HANDLE AND COVER

BACKGROUND OF THE INVENTION

One type of buccal hygiene apparatus includes a casing enclosing a hydraulic pump and motor unit. A handpiece is connected to the casing by a flexible tubing. A reservoir is removably fittable on the casing in a position for supplying water to the pump and motor unit via an outlet in the bottom of the reservoir. The outlet has a valve for closing it when the reservoir is fitted on the casing.

In that type of apparatus, the handpiece can receive a spray head which delivers a jet of pulsated water for cleaning the teeth and massaging the gums. In some "combined" apparatus, the spray nozzle can be replaced by a toothbrush which is oscillated by a hydraulic motor housed in the handpiece. In both of these conventional types of devices, the reservoir supplies water to the pump and motor unit independent of the water supply.

In general, the reservoir is provided to perform a dual purpose, as a water-supply reservoir and, when emptied of water and turned up the other way, as a cover or lid for the apparatus when it is not in use. Because of this fact, the conventional reservoirs must be sufficiently large to fit on and cover the housing.

This feature often proves to be a disadvantage due to the relatively large dimensions of the reservoir which make it clumsy to handle for the purpose of filling the water and, when it is filled with water, it is not always easy to correctly fit it, the first time, on the housing with its outlet coinciding with the pump inlet. These disadvantages become particularly noticeable when the apparatus is used by children when they experience difficulty in holding the reservoir in one hand. The reservoir may thus be held in both hands, or by its upper rim, with a thumb extending into the reservoir, and this in unhygienic.

SUMMARY OF THE INVENTION

The present invention proposes to remedy the above discussed disadvantages and to provide an apparatus of the general type described above which is easy to manipulate.

To this end, the buccal hygiene apparatus according to the invention is characterized in that the reservoir is provided with a gripping member, and the reservoir is of smaller dimensions than the casing.

In an apparatus according to the invention, the sole function of the reservoir is to store the water, or other liquid for a buccal treatment, and, as the reservoir does not form a lid, it can be of relatively small dimensions.

It is hence easier to handle, even by children, because of its reduced dimensions and the provision of a gripping member. Such a reservoir may have a content of ½ liter to 1 liter of water, which is quite sufficient for the buccal treatment in question.

In a preferred embodiment, the gripping member is a handle protruding from the face of the reservoir, and the reservoir is provided with a lid having a projection disposed adjacent the handle and serving for opening of the lid.

Another preferred feature of the invention is that one of the walls of the reservoir has in its upper part an opening limiting the water level.

Another preferred feature of the invention, among others, is that the reservoir wall has a forwardly projecting profile which fits in a complementary profile in the facing wall of the casing to facilitate the exact placing of the reservoir on the casing.

BRIEF DISCRIPTION OF THE DRAWINGS

Two embodiments of the invention are shown, by way of example, in the accompanying drawings, in which:

FIG. 3 is a sectional elevation view thereof taken along the plane of line 3—3 of FIG. 2;

FIG. 4 is a top sectional view thereof taken along the plane of line 4—4 of FIG. 3;

DESCRIPTION OF THE PREFERRED EMBODIMENTS

Figure 1:
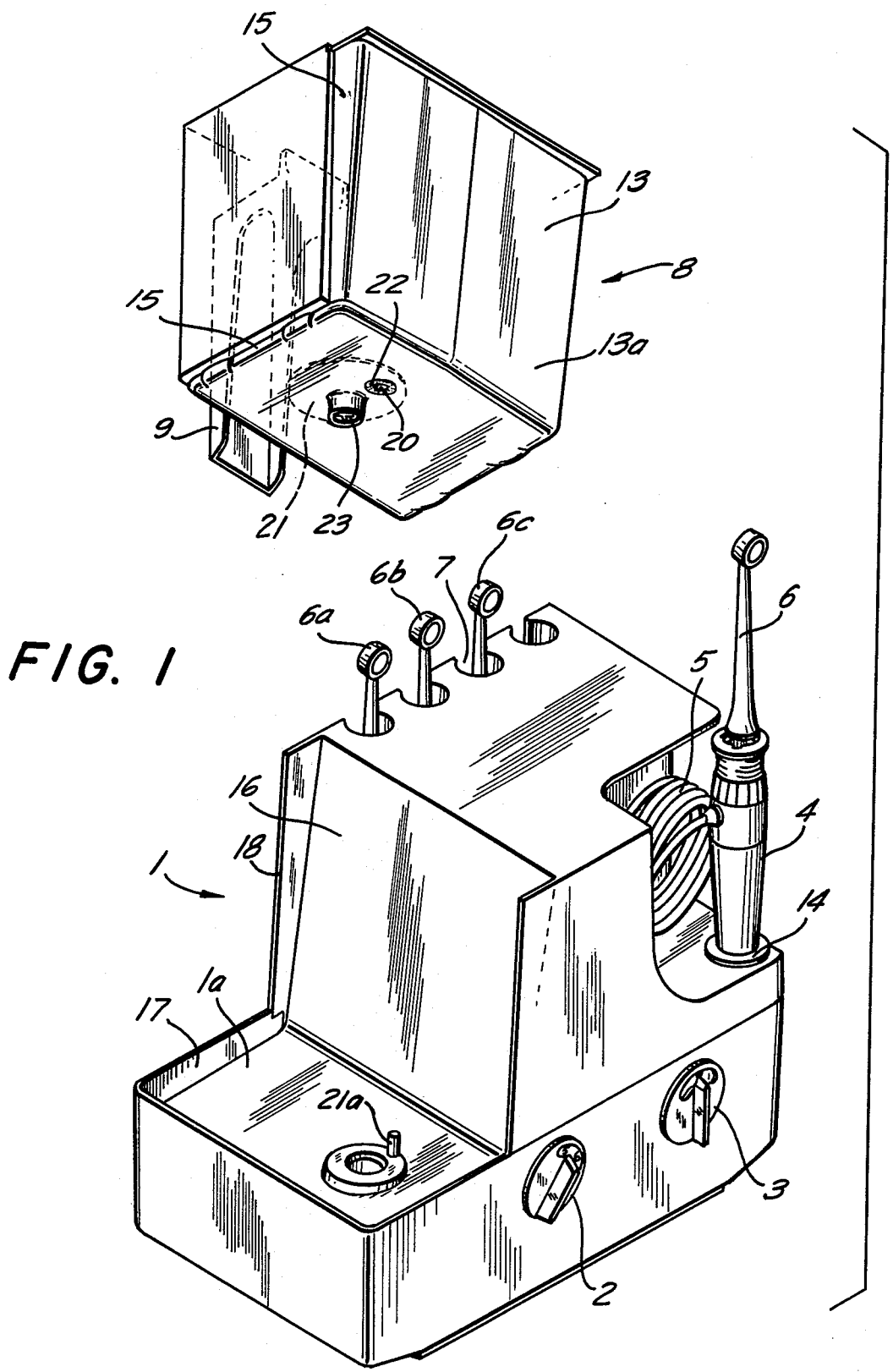
FIG. 1 is an exploded perspective view of the apparatus with one spray head connected to the handpiece and several spare spray heads on the housing.

The apparatus of FIGS. 1-4 consist of a casing 1 which contains a hydraulic pump of a conventional nature and, therefore, only external control buttons 2 and 3 are shown. A handpiece 4 is held vertically in a recess 14 of casing 1, and is connected by a flexible tube 5 to the hydraulic pump. On the handpiece 4 is fitted a spray head 6, and several spare interchangeable spray heads 6a, 6b, and 6c are stored upstanding in suitable housings 7 in casing 1.

Casing 1 has a lateral projecting part defining a shelf 1a adapted to receive a removable reservoir 8. On one of its lateral faces, the reservoir 8 has a handle 9 fixed to the upper part of the reservoir, and serving for gripping and carrying the reservoir. A lid 10 is connected by a hinge 11 to the reservoir 8 and has, adjacent the handle 9, an upstanding projection 12 which enables the lid 10 to be opened by the thumb of the hand holding handle 9.

In the illustrated embodiment of FIGS. 1-4, the handle 9 projects from the reservoir, and hence from the assembled apparatus, and is formed in a single piece with the reservoir 8. As a variation, as shown in FIG. 5 and 6, the handle 9a can be flush with the outer wall 10a of the reservoir 8a, and a recess 24 is provided in the reservoir wall to accomodate the hand holding the handle.

The shape of the reservoir 8 of FIGS. 1-4 is such that, when fitted, three of its side faces are flush with and in extension of the corresponding faces of the casing 1, and the lid 10 in its rest position is in the same plane as the upper face of casing 1. The fitted reservoir 8 and casing 1 thus forms a compact unit.

Figure 5:
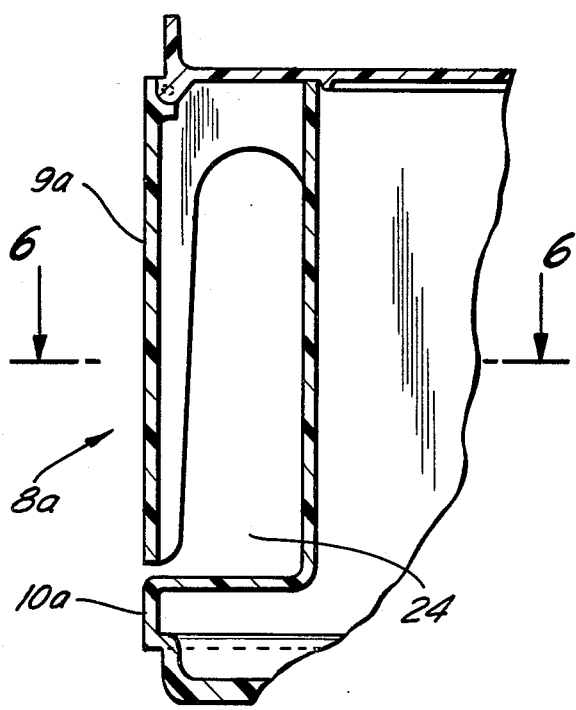
FIG. 5 is a fragmentary side elevation view of a portion of the reservoir of the apparatus showing an alternative form of handle.
Figure 6:
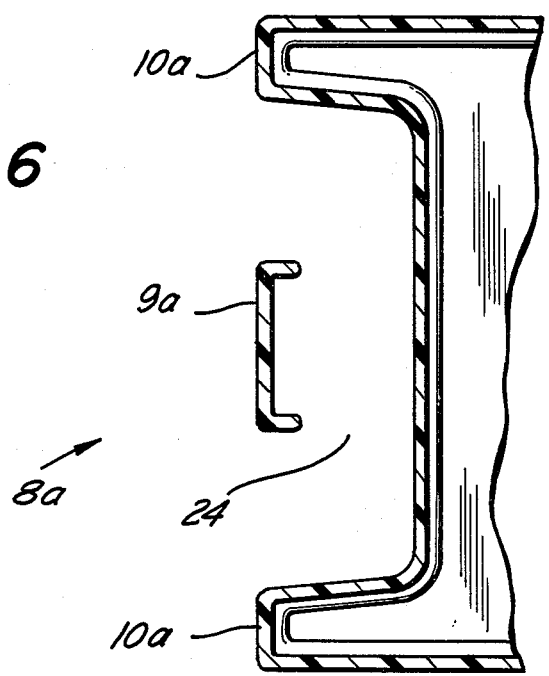
FIG. 6 is a top sectional view thereof taken along the plane of line 6—6 of FIG. 5.

The embodiment of FIGS. 5 and 6 provide a further feature adding to the compactness of the reservoir by recessing the handle thereby providing a fourth substantially flush side to the reservoir.

To permit exact positioning and rapid fitting of the reservoir 8 on casing 1, its side face opposite handle 9 has an advanced projecting profile 13 which extends to form the bottom of the reservoir. The front part 13a of this profile is inclined and at its edges has parts 15 generally in extension of, but inset from, the corresponding main parts of the lateral walls of reservoir 8. The same applies to the bottom of the reservoir. The casing 1 has a corresponding recessed wall 16 of the same profile, with lateral projections 17, 18 complementary to parts 15 of reservoir 8 which cooperate with the parts 15 to facilitate insertion of the reservoir in its housing, and firmly seat the reservoir in its assembled position. These mating parts also provide for indexing of the valve means on the reservoir and on the casing to provide for cooperative interacting between the reservoir and casing in the manner described below. The general arrangement also provides the apparatus with a pleasing aesthetic appearance.

Figure 2:
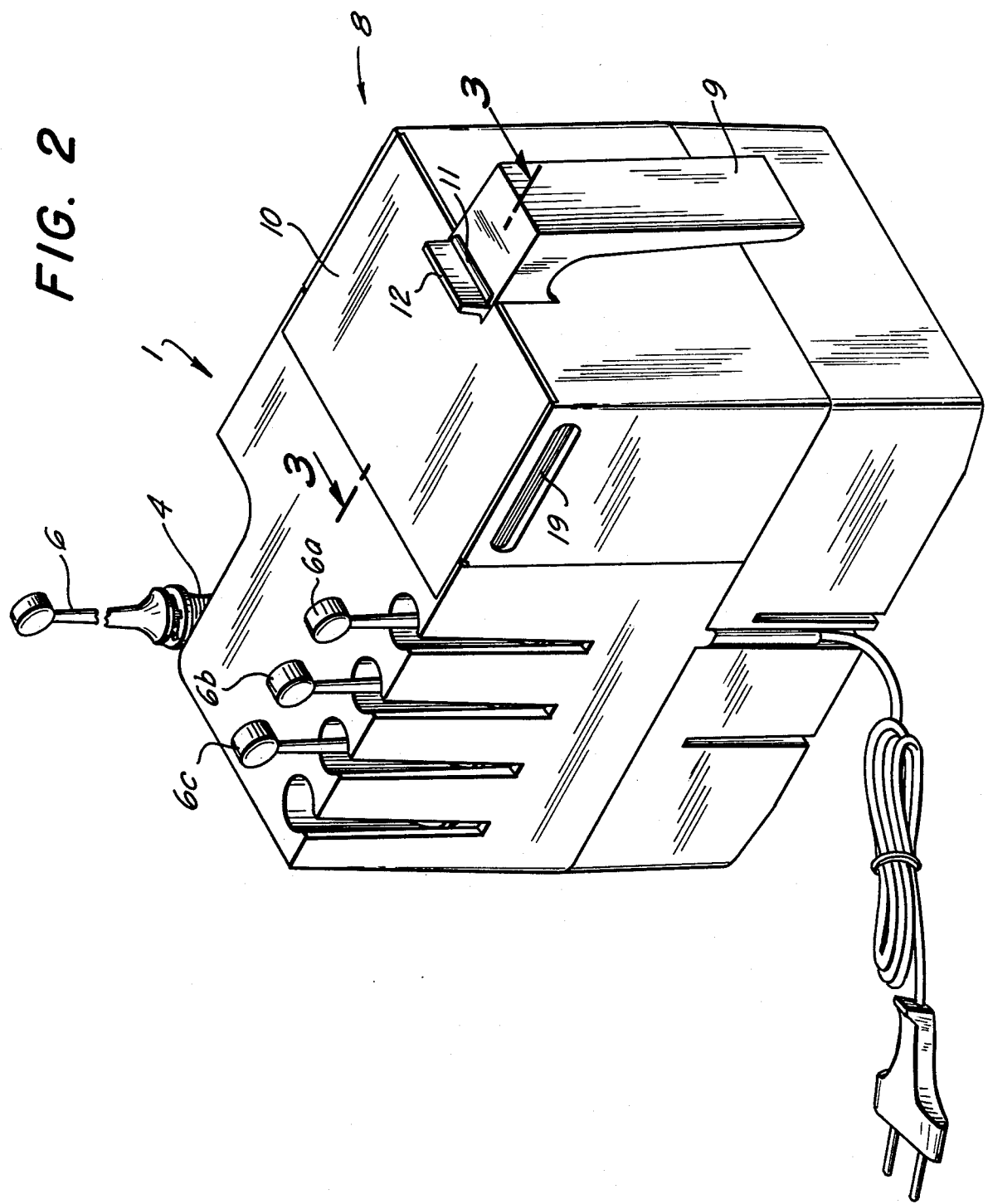
FIG. 2 is a perspective view thereof in assembled condition.

As shown in FIG. 2, one of the lateral faces of reservoir 8 has an overflow slot 19 which prevents the user from overfilling the reservoir and reduces spilling of water when the full reservoir is being carried.

In the bottom of the reservoir is an elastically-deformable stud 20, eccentrically disposed to a circular flap valve 21, and cooperating with a part 21a of the casing 1 to lift up the flap valve 21 when the reservoir is seated on the casing. Stud 20 is fluid-tightly mounted in a hole 22 in the bottom of the reservoir spaced apart from a hole 23 in which the flap valve 21 is fitted. In that manner, closing of the reservoir 8 in seated and indexed position within casing 1 automatically causes part 21a to extend into stud 20 and open flap valve 21 to permit fluid to flow from the reservoir into the casing. Similarly, when the reservoir is removed and part 21a is removed from stud 20, the flap valve will once again seat and close opening 23 preventing fluid from exiting from the bottom of reservoir 8.

Thus the several aforenoted objects and advantages are most effectively attained. Although several somewhat preferred embodiments have been disclosed and described in detail herein, it should be understood that this invention is in no sense limited thereby and its scope is to be determined by that of the appended claims.

I claim:

1. A buccal hygiene apparatus comprising a casing enclosing a hydraulic pump and motor unit, a handpiece connected to the casing by a flexible tubing, and a reservoir removably fitable on the casing in a position for supplying water to the pump and motor unit via an outlet in the bottom of the reservoir, said outlet having valve means for closing it when the reservoir is removed from the casing and opening it when the reservoir is fitted on the casing, characterized in that the reservoir is of smaller dimensions than the casing, a gripping member is provided on the reservoir, a lid is provided on the reservoir having a projection adjacent the gripping member to enable opening of the lid by the thumb of a hand holding the gripping member, and a slot is provided in the upper part of one of the walls of the reservoir to prevent overflow and reduce spilling, said slot being defined by portions of one of the walls of the reservoir, the wall portions completely surrounding the slot.

2. Apparatus according to claim 1, in which the reservoir has lateral walls which, when the reservoir is fitted on the casing, extend in alignment with corresponding lateral walls of the casing.

3. Apparatus according to claim 2, in which the reservoir has a lid which when closed extends in alignment with an upper face of the casing.

4. Apparatus according to claim 1, comprising guide means for positioning the reservoir on the casing.

5. Apparatus according to claim 4, in which said guide means comprises a forwardly projecting profile of the reservoir which fits in a complementary profile of a facing part of the casing, said casing having a lateral part defining a shoulder on and in which the reservoir is seated.

6. A buccal hygiene apparatus comprising a casing enclosing a hydraulic pump and motor unit, a handpiece connected to the casing by a flexible tubing, and a reservoir removably fittable on the casing in a position for supplying water to the pump and motor unit via an outlet in the bottom of the reservoir, said outlet having valve means for closing it when the reservoir is removed from the casing and opening it when the reservoir is fitted on the casing, characterized in that the reservoir is of smaller dimensions than the casing, a gripping member is provided on the reservoir, a lid is provided on the reservoir having a projection adjacent the gripping member to enable opening of the lid by the thumb of a hand holding the gripping member, a slot is provided in the upper part of one of the walls of the reservoir to prevent overflow and reduce spilling, said slot being defined by portions of one of the walls of the reservoir, the wall portions completely surrounding the slot, and further comprising an elastically-deformable member mounted in the bottom of the reservoir eccentric to an axis of said valve means, said deformable member cooperating with a part of the casing to lift up said valve means.

* * * * *

UNITED STATES PATENT OFFICE
CERTIFICATE OF CORRECTION

PATENT NO. : 4,109,650
DATED : August 29, 1978
INVENTOR(S) : MICHEL PECLARD

It is certified that error appears in the above—identified patent and that said Letters Patent are hereby corrected as shown below:

Column 1, line 11, after "is" insert --removed from the casing and opening it when the reservoir is--.

Signed and Sealed this

Tenth Day of April 1979

[SEAL]

Attest:

RUTH C. MASON
Attesting Officer

DONALD W. BANNER
Commissioner of Patents and Trademarks